US011292923B2

(12) United States Patent
Tate et al.

(10) Patent No.: US 11,292,923 B2
(45) Date of Patent: Apr. 5, 2022

(54) COMPOSITE RESINS CONTAINING SILVER NANOPARTICLES

(71) Applicant: INHIBIT COATINGS LIMITED, Wellington (NZ)

(72) Inventors: Eldon Warwick Tate, Wellington (NZ); James Howard Johnston, Wellington (NZ)

(73) Assignee: INHIBIT COATINGS LIMITED, Wellington (NZ)

( * ) Notice: Subject to any disclaimer, the term of this patent is extended or adjusted under 35 U.S.C. 154(b) by 0 days.

(21) Appl. No.: 16/817,715

(22) Filed: Mar. 13, 2020

(65) Prior Publication Data

US 2020/0239709 A1  Jul. 30, 2020

Related U.S. Application Data

(63) Continuation of application No. 16/612,564, filed as application No. PCT/NZ2018/050066 on May 10, 2018.

(30) Foreign Application Priority Data

May 12, 2017  (NZ) ........................................ 731844

(51) Int. Cl.
| | |
|---|---|
| C09D 5/16 | (2006.01) |
| C09D 5/14 | (2006.01) |
| C09D 7/61 | (2018.01) |
| C09D 133/12 | (2006.01) |
| C09D 163/00 | (2006.01) |
| C09D 175/04 | (2006.01) |
| C08K 3/08 | (2006.01) |

(52) U.S. Cl.
CPC ............ *C09D 5/1618* (2013.01); *C09D 5/14* (2013.01); *C09D 7/61* (2018.01); *C09D 133/12* (2013.01); *C09D 163/00* (2013.01); *C09D 175/04* (2013.01); *C08K 2003/0806* (2013.01); *C08K 2201/011* (2013.01)

(58) Field of Classification Search
CPC .......................... C09D 7/61; C08K 2003/0806
See application file for complete search history.

(56) References Cited

U.S. PATENT DOCUMENTS

| | | | | |
|---|---|---|---|---|
| 8,101,680 | B1* | 1/2012 | Ramakrishan | ........... C08J 3/201 |
| | | | | 524/431 |
| 8,779,023 | B2* | 7/2014 | Whang | .................. A01N 59/16 |
| | | | | 523/113 |
| 2010/0120942 | A1 | 5/2010 | Ajayan et al. | |
| 2011/0020170 | A1* | 1/2011 | Luinstra | ................... C01G 7/00 |
| | | | | 420/463 |
| 2011/0024699 | A1* | 2/2011 | Lin | ..................... C08F 222/08 |
| | | | | 252/514 |
| 2011/0180764 | A1* | 7/2011 | Takahashi | ................. C09C 1/62 |
| | | | | 252/514 |
| 2011/0256383 | A1* | 10/2011 | Cochet | ..................... C08K 3/10 |
| | | | | 428/328 |
| 2011/0306699 | A1* | 12/2011 | Whang | ................... A61L 27/54 |
| | | | | 523/113 |
| 2014/0024773 | A1* | 1/2014 | Gong | ....................... C08K 9/04 |
| | | | | 524/724 |
| 2014/0220366 | A1* | 8/2014 | Wang | ....................... H01B 1/22 |
| | | | | 428/457 |
| 2015/0203700 | A1* | 7/2015 | Lee | ....................... B22F 1/0062 |
| | | | | 106/31.92 |
| 2016/0122499 | A1* | 5/2016 | Farrugia | .................. C08K 3/08 |
| | | | | 524/440 |
| 2016/0255839 | A1* | 9/2016 | Whang | ................... A61L 15/24 |
| 2016/0274460 | A1* | 9/2016 | Brust | ....................... C09D 7/68 |
| 2016/0274461 | A1* | 9/2016 | Brust | ....................... B05D 7/04 |
| 2017/0181439 | A1* | 6/2017 | Achilias | ................. A01N 25/28 |
| 2017/0298232 | A1* | 10/2017 | Farrugia | ............ C08G 63/6886 |
| 2017/0342279 | A1* | 11/2017 | Kawamura | .............. C09D 5/24 |
| 2018/0354031 | A1* | 12/2018 | Izumi | .................. H01M 4/0471 |

FOREIGN PATENT DOCUMENTS

| | | |
|---|---|---|
| KR | 10-2014-0115497 A | 10/2014 |
| WO | 2014/052973 A1 | 4/2014 |

OTHER PUBLICATIONS

Bogdanova et al. (Polymer Science, Ser. A, 2014, vol. 56, No. 3, pp. 304-310) (Year: 2014).*
Cahill et al., Laboratory assessment of the antifouling potential of a soluble-matrix paint laced with the natural compound polygodial, Biofouling, 29:967-975 (2013).
Chen et al., Silver nanoparticles capped by oleylamine: formation, growth, and selforganization, Langmuir, 23:5296-5304 (2007).
Cheng et al., In situ fabrication of photocurable conductive adhesives with silver nano-particles in the absence of capping agent, Int. J. Adhes. Adhes., 27:236-243 (2007).
Cheng et al., In situ formation of silver nanoparticles in photocrosslinking polymers, J. Biomed. Mater. Res. B. Appl. Biomater., 97:124-131 (2011).
Hoppe et al., One-step synthesis of gold and silver hydrosols using poly(N-vinyl-2-pyrrolidone) as a reducing agent, Langmuir, 22:7027-7034 (2006).
International Application No. PCT/NZ2018/050066, International Preliminary Report on Patentability, dated Nov. 21, 2019.
International Application No. PCT/NZ2018/050066, International Search Report and Written Opinion, dated Jul. 16, 2018.
Kim et al., Synthesis of poly(urethane acrylate-co-styrene) films containing silver nanoparticles by a simultaneous copolymerization/ in situ electron transfer reaction, Macromol. Chem. Phys., 206:794-801 (2005).

(Continued)

*Primary Examiner* — Liam J Heincer
(74) *Attorney, Agent, or Firm* — Marshall, Gerstein & Borun LLP

(57) ABSTRACT

A composite resin comprising silver nanoparticles and a polymer where the silver nanoparticles are formed by reduction of silver ions by the functional groups of the polymer without the addition or application of an external reducing agent. The composite e resin has a low silver leach rate. The composite resin may be used as a surface coating, particularly an antimicrobial or antifouling surface coating.

10 Claims, 3 Drawing Sheets

(56) References Cited

OTHER PUBLICATIONS

Kumar et al., Silver-nanoparticle-embedded antimicrobial paints based on vegetable oil, Nat. Mater., 7(3):236-241 (2008).
Lee et al., Adsorption and surface-enhanced raman of dyes on silver and gold sols, J. Phys. Chem., 60439:3391-3395 (1982).
Maciollek et al., One pot synthesis of silver nanoparticles using a cyclodextrin containing polymer as reductant and stabilizer, Beilstein J. Nanotechnol., 5:380-385 (2014).
Naik et al., Synthesis of silver nanoparticles embedded novel hyperbranched urethane alkyd-based nanocomposite for high solid antimicrobial coating application, J. Coat. Technol. Res., 12(6):1073-1083 (2015).
Perry, M., Nanogold and Nanosilver Hybrid Polymer Materials, A thesis submitted to the Victoria University of Wellington (2013).
Sangermano et al., In situ synthesis of silver-epoxy nanocomposites by photoinduced electron transfer and cationic polymerization processes, Macromolecules, 6:8827-8829 (2007).
Silva et al., Silver nanoparticle in situ growth within crosslinked poly(ester-co-styrene) induced by UV irradiation: aggregation control with exposure time, J. Phys. Chem. Solids, 68:729-733 (2007).
Xiong et al., Poly(vinyl pyrrolidone): a dual functional reductant and stabilizer for the facile synthesis of noble metal nanoplates in aqueous solutions, Langmuir, 22:8563-8570 (2006).
Zhang et al., Hyperbranched Poly(amidoamine) as the Stabilizer and Reductant to Prepare Colloid Silver Nanoparticles in Situ and Their Antibacterial Activity, Phys. Chem. C, 112(7):2330-2336 (2008).

\* cited by examiner

COMPOSITE RESINS CONTAINING SILVER NANOPARTICLES

CROSS-REFERENCE TO RELATED APPLICATIONS AND INCORPORATION BY REFERENCE

This application is a continuation of U.S. patent application Ser. No. 16/612,564, filed Nov. 11, 2019, which in turn is a U.S. national phase pursuant to 35 U.S.C. § 371 of International Patent Application No. PCT/NZ2018/050066, filed May 10, 2018, which claims priority to NZ Patent Application No. 731844, filed May 12, 2017, the disclosures of which are all herein incorporated by reference in their entireties.

TECHNICAL FIELD

The invention relates to composite resins containing silver nanoparticles. In particular, the invention relates to a method for producing such composite resins that avoids the need to use an external reducing agent for reducing silver ions to metallic silver nanoparticles. This leads to composites having superior properties. The invention also relates to the use of composite resins as antifouling and antimicrobial coatings.

BACKGROUND OF THE INVENTION

Nanocomposite materials can impart new and useful functionality to otherwise inane substrates. These materials are often sought after in applications such as biosensors, medical devices and photocatalysis. Of particular interest is the area of antimicrobials and antifouling. Silver and silver salts are well-known antimicrobial agents. The antimicrobial effects of silver and silver salts are enhanced when they are in the nano size range.

The Turkevich method is a well-researched dual reductant stabiliser method for producing gold nanoparticles. The method uses trisodium citrate (TSC) to both reduce and then stabilise the resulting nanoparticles. While traditionally used for gold nanoparticle synthesis, the method was extended to silver by Lee in 1982.[1] In this method, TSC is added to a solution of $AgNO_3$ under heat while mixing. Under these reaction conditions, TSC undergoes decarboxylation reducing the $Ag^+$ to $Ag^0$. Once $Ag^0$ nanoparticles are formed they are capped and stabilised by the carboxylic functionality of the TSC which prevents agglomeration.

Polyvinylpyrrolidone (PVP) was considered for a long time as just a simple polymer stabilising agent. However, PVP has been shown to act as a dual reductant and stabiliser. The mechanism of reduction has been postulated to occur via different routes. One route is by oxidation of the terminal hydroxyl groups and the other route is via a free radical mechanism.[2,3] In the free radical mechanism, it is assumed that metal ion reduction potential is strong enough to abstract protons directly from the allylic or tertiary carbons of the polymers. Proton abstraction from either of these carbons forms radical breakdown products, which can also be directly involved in the further reduction of metal ions in solution to grow silver nanoparticles. The PVP then acts as a stabilising agent to prevent agglomeration of the silver nanoparticles in solution.

Polymers containing an amino functionality have also proved to be dual reductants and stabilisers for the synthesis of colloidal noble metal nanoparticles. In a similar manner to PVP oxidation of the hydroxyl groups, primary and secondary amine functional groups can undergo oxidative dehydrogenation promoted by the metal ions, and in the process form silver nanoparticles. One specific example is the formation of silver nanoparticles by oleylamine in paraffin.[4] The mechanism involves the formation of a complex of the silver ions with the amine functionality of the oleylamine. This then leads to one-electron transfer from the amines to silver ions, generally at high temperatures, and the formation of amino radicals and simultaneous reduction of silver ions to metallic silver. The amino radicals then undergo deprotonation to form imines, or the process continues on further to form nitriles. The imines and nitriles, along with excess amines in solution, then stabilise the resulting silver nanoparticles.

Silver nanoparticle polymer composites have had a strong focus in materials science research in recent years. The plethora of applications for surface coatings and plastics with antimicrobial ability and the strong antimicrobial behaviour of silver make them a very promising avenue as functional polymers. The scientific literature has many examples of silver nanoparticles being formed or added to polymers to make composite materials. However, these methods generally use either pre-synthesised nanoparticles simply blended into the formulation or additional reducing agents to form the nanoparticles. These two methods of silver nanocomposite synthesis have limitations in the properties of the polymers that can be achieved.

A common method for the formation of silver nanoparticles in situ utilises UV light as an external reducing agent. The photosensitivity of silver ions is well-known, and forms the basis of black and white photography. In order to take advantage of this characteristic, UV-curable systems, such as poly(ester-co-styrene) resins, have $AgNO_3$ added to the resin. A high energy arc lamp then irradiates the resin and initiates cross-linking of the resin while simultaneously photoreducing the $AgNO_3$ to metallic silver.[5] Similarly, silver nanoparticle epoxy-acrylic resins have been synthesised through the addition of $AgNO_3$ to ethylene glycol followed by irradiation with UV light to form silver nanoparticles within the resin through the photoreduction of silver ions.[6] In these cases, the reduction of silver ions is carried out using the high energy UV light, and the stabilisation of the silver nanoparticles occurs by trapping within the resin during curing.

A mechanism that is comparable to UV photoreduction of silver ions to metallic silver nanoparticles within resins is the use of photoinitiators to form radical species that initiate the reduction of silver ions, as well as propagating the radical cross-linking of the resin. Typically, this approach utilises silver hexafluoroantimonate ($AgSbF_6$), as this improves radical cationic curing in the epoxy systems.[7] Again, the silver nanoparticles are formed by external reducing species, the radical initiator, then trapped within the resin as it cross-links. Kim et al. showed that in situ electron transfer for the reduction of silver to form silver nanoparticles could be coupled with the copolymerisation of styrene and urethane acrylate non-ionmer by the addition of silver salts and the radical initiator 2,20-azoisobutyronitrile (AIBN) to the system.[8]

Cross-linked methacrylate polymers with silver nanoparticles have been synthesised using photoinitiated radical polymerisation of dimethacrylates with in situ silver ion reduction.[9] These cases use a radical initiator which requires UV light to generate radical species to form the nanoparticles within the polymer systems. These methods, while forming the silver nanoparticles in situ within the resin, take advantage of the reducing power of photoinitiators or UV light, not the polymer itself, to reduce the silver ions to metallic silver.

The above systems that utilise UV photoreduction or free radical initiated reduction to form silver nanoparticles within the composite have shown promise in antimicrobial applications. However, due to these systems simply encapsulating the nanoparticles, they have the potential to leach significant amounts of silver during the lifetime of the composites.

United States patent publication U.S. 2010/0120942 describes the synthesis of metal and metal oxide nanoparticle-embedded siloxane composites. The synthesis method is an in situ method using a polymerising agent to reduce metal salts to metal particles. The method does not require any external reducing or stabilizing agent. The polymerising agent, often under high temperatures, generates radicals which then reduce silver ions to metallic silver, similarly to methods incorporating radical initiators. Thus, polymerisation takes place at the same time or before formation of silver nanoparticles. This means that there is likely to be relatively weak binding between the nanoparticles and the polymer backbone resulting in areas of high agglomeration or poor dispersion of nanoparticles in the polymer matrix, poor stability of the polymer, leaching over time of metallic silver, and reduced effectiveness and lifetime of the material, for example as an anti-microbial coating.

The applicant has now found a new synthesis methodology that overcomes or ameliorates disadvantages of the abovementioned methodologies. The synthesis methodology developed uses the polymer as a dual reductant and stabiliser, and involves the formation of silver nanoparticles by the polymer and in the polymer before polymerisation occurs. This facilitates a strong interaction between the silver nanoparticles and the polymer, and in turn yields a non-leaching or low leaching composite material with an extended antimicrobial life, without compromising the properties of the polymer itself. This is unlike materials that form nanoparticles using external reducing agents where the nanoparticles are poorly bound or incorporated into the polymer matrix.

It is therefore an object of the invention to provide a composite resin containing silver nanoparticles that is useful for a range of applications including antimicrobial or antifouling coatings, or to at least provide a useful alternative to existing resins.

SUMMARY OF THE INVENTION

In a first aspect of the invention there is provided a composite resin comprising:
(i) silver nanoparticles; and
(ii) a polymer having functional groups capable of interacting with at least some of the silver nanoparticles to prevent or minimise agglomeration of silver nanoparticles;
wherein the silver nanoparticles are formed by reduction of silver ions by the functional groups of the polymer without the addition or application of an external reducing agent.

In some embodiments of the invention the functional groups of the polymer are ester, ether, amine, imine, nitrile, epoxide, carboxyl, hydroxyl, or carboxylic acid groups. The polymer is preferably an acrylic, polyol, amine, or epoxy polymer. Examples of the polymer include methyl acrylate, ethyl acrylate, butyl acrylate, methyl methacrylate, butyl methacrylate, acrylonitrile, polyether polyol, polyester polyol, polyol, polyamine, bisphenol A epoxy and bisphenol F epoxy polymers.

The composite resin of the invention is formed without the application of UV light or heating at a temperature of 100° C. or greater, or the addition of an external reducing agent such as trisodium citrate, sodium borohydride, hydroxylamine hydrochloride, hydrazine, ascorbic add, ethylenediaminetetraacetic add (EDTA), polyvinylpyrrolidone, dimethylformamide, a plant extract, hydrogen gas, or a radical initiator, In preferred embodiments of the invention, the silver nanoparticles are stabilised to prevent or minimise agglomeration of silver nanoparticles without the addition of an external stabiliser. Examples of such stabilisers include trisodium citrate, polyvinylpyrrolidone, polyvinyl alcohol, oleylamine, cetyl trimethylammonium bromide, poly(N-isopropylacrylamide), sugars, fatty acids, and sodium dodecyl sulfate.

In a second aspect the invention provides a method for preparing a composite resin containing silver nanoparticles comprising contacting a polymer having reducing functional groups with a solution of silver ions where at least some of the silver ions are reduced to metallic silver nanoparticles, provided that no external reagent for reducing silver ions to metallic silver nanoparticles is added or applied. The silver nanoparticles are also stabilised and bound within the polymer matrix without the addition of stabilising or coupling agents.

In some embodiments of the invention the silver ions are in the form of a solution of silver nitrate, silver acetate, silver carbonate, silver perchlorate, silver phosphate, silver trifluoroacetate, silver benzoate, or silver lactate.

In another aspect the invention provides the use of a composite resin of the invention as an antimicrobial coating. In some embodiments, the antimicrobial coating is an antibacterial coating, for example a surface coating on a medical device, a heating ventilation unit, an air-conditioning unit, air or fluid ductwork, a water reservoir, a wall, floor or ceiling, or food and beverage manufacturing equipment or packaging.

In another aspect the invention provides the use of a composite resin of the invention as an antifouling coating. In some embodiments, the antifouling coating is a coating on a surface submerged in water, for example all or part of a vessel hull, a jetty or wharf structure, off-shore platform or aquaculture equipment.

In another aspect the invention provides a composite resin for coating a surface comprising:
(i) silver nanoparticles; and
(ii) a polymer having functional groups capable of interacting with at least some of the silver nanoparticles to prevent or minimise agglomeration of silver nanoparticles;
wherein the resin has a silver leach rate of less than 1 part per billion per $cm^2$ per day ($ppb/cm^2/day$).

In some embodiments of the invention the silver leach rate is less than 0.1 or 0.01 $ppb/cm^2/day$.

In some embodiments of this aspect of the invention the functional groups of the polymer are ester, ether, amine, imine, nitrile, epoxide, carboxyl, hydroxyl, or carboxylic acid groups. The polymer is preferably an acrylic, polyol, amine, or epoxy polymer. Examples of the polymer include methyl acrylate, ethyl acrylate, butyl acrylate, methyl methacrylate, butyl methacrylate, acrylonitrile, polyether polyol, polyester polyol, polyol, polyamine, bisphenol A epoxy and bisphenol F epoxy polymers.

The composite resin of the invention is formed without the application of UV light or heating at a temperature of 100° C. or greater, or the addition of an external reducing agent such as trisodium citrate, sodium borohydride, hydroxylamine hydrochloride, hydrazine, ascorbic add, ethylenediaminetetraacetic add (EDTA), polyvinylpyrrolidone, dimethylformamide, a plant extract, hydrogen gas, or a radical initiator, In preferred embodiments of the invention, the silver nanoparticles are stabilised to prevent or minimise agglomeration of silver nanoparticles without the addition of an external stabiliser. Examples of such stabilisers include trisodium citrate, polyvinylpyrrolidone, polyvinyl alcohol, oleylamine, cetyl trimethylammonium bromide, poly(N-isopropylacrylamide), sugars, fatty acids, and sodium dodecyl sulfate.

DETAILED DESCRIPTION

Figure 1:
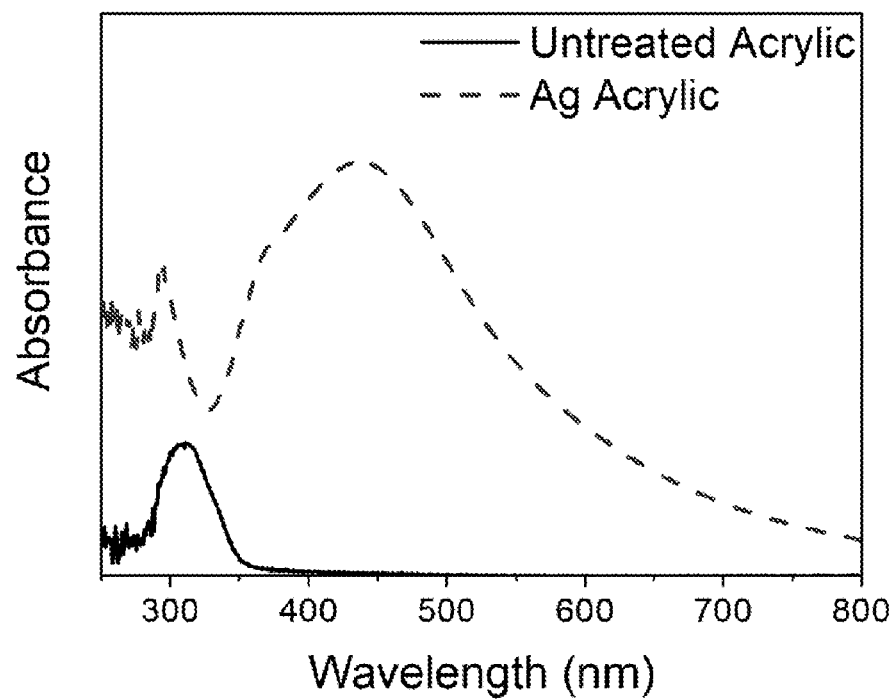
FIG. 1 shows UV-vis spectra of untreated and Ag functionalised Neocryl™ XK-98.
Figure 2:
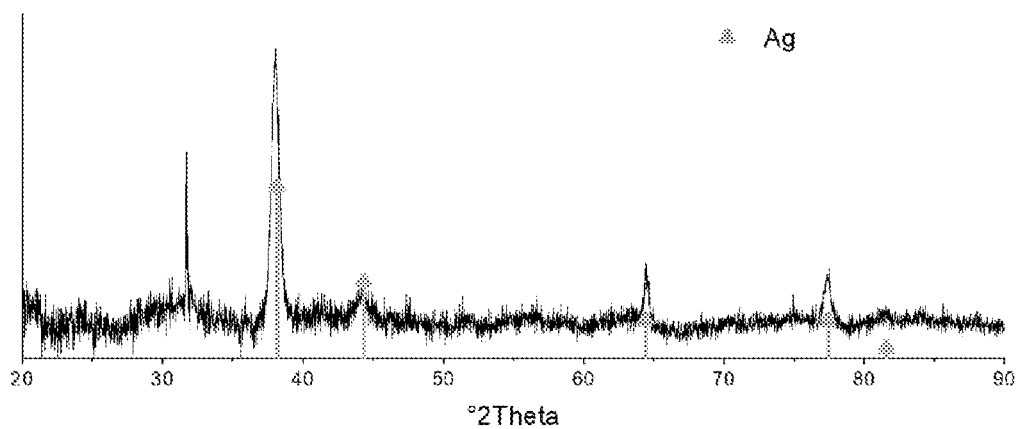
FIG. 2 shows an XRD pattern of Ag functionalised Neocryl™ XK-98.

The invention uses a novel in situ approach to form silver nanoparticles and bind them to a polymer without the need for an external reducing agent. This method uses the functionality of the polymer itself to reduce $Ag^+$ to metallic Ag nanoparticles and to create antimicrobial and antifouling polymers and polymer resin coatings. The invention utilises the inherent functionality of the polymer to act as a dual reductant and stabiliser. Stabilisation of the Ag nanoparticles formed is necessary to ensure dispersion of the nanoparticles throughout the polymer matrix. Otherwise, agglomeration of the nanoparticles occurs leading to reduced or absent antimicrobial activity. Insufficient stabilisation of nanoparticles also leads to leaching of Ag, which has an adverse environmental impact and a decreasing antimicrobial activity of the composite over time.

The term "nanoparticle" means any particle having at least one dimension, e.g. diameter, in the range of several nanometres to several hundred nanometres.

The term "composite" means a material made from two or more constituent materials with different physical or chemical properties that produce a material with characteristics different from the individual constituent materials when combined, The term "resin" means a solid or liquid non-crystalline natural or synthetic organic polymeric compound capable of being used as a coating on a surface or being formed into an article or a coating on the surface of an article, Resins include paints, varnishes, stains, waxes and other types of coating materials.

The term "reducing agent" means a compound or substance that loses (or donates) an electron to another chemical species in a redox chemical reaction and as a consequence reduces the oxidation state of that chemical species.

The term "external reducing agent" means a reducing agent that has been added or applied from an external source.

The term "functional group" means a group of atoms or bonds responsible for the characteristic reactions of a particular compound.

The term "agglomeration" means the action or process of clustering or grouping of matter.

The term "stabiliser" means an additive that helps maintain the structure of a composite where silver particles are dispersed throughout the composite and minimises agglomeration of the silver particles.

The invention takes advantage of the chemical functionality of the polymer used in the formulation to form silver nanoparticles in situ. Silver nanoparticles are well-known antimicrobial agents and can prevent the growth and proliferation of microbes and thereby protect surfaces from contamination. Unlike known methods of creating silver nanoparticles where nanoparticles are synthesised ex situ followed by coupling or mixing, or nanoparticles are formed in situ utilising external reducing agents or heating, the method of the present invention uses no external reducing agent, cross-linker, UV or radical initiator to form the nanoparticles. The method of the invention uses only the chemical functionality of the polymer itself.

The strong association of nanoparticles with the polymer backbone of composites leads to advantages over other Ag nanoparticle polymer composites. The composites have a very low leach rate of Ag which avoids the problem of silver simply washing out of the material during use. The leach rate of Ag has been found by the applicant to be less than about 1 part per billion per $cm^2$ per day ($ppb/cm^2/day$). This is considered to be due to the strong association between Ag nanoparticles and functional groups of the polymer backbone which form. The strong associations, which may be covalent bonds or other types of interactions, appear to be a direct result of formation of the Ag nanoparticles by reduction of silver ions by functional groups of the polymer. The same strong associations are not observed when an external reducing agent is used for Ag nanoparticle formation.

The composite resins of the invention have Ag nanoparticles well-dispersed which leads to high antimicrobial and antifouling activity, without degrading the physical characteristics of the polymer/coating itself. This is unlike additive based composites where addition of the antimicrobial component can decrease the physical properties of the polymer/coating, lowering hardness, abrasion resistance, viscosity and affect film formation.

The invention provides a composite resin comprising silver nanoparticles and a polymer having functional groups capable of interacting with at least some of the silver nanoparticles to prevent or minimise agglomeration of silver nanoparticles. The silver nanoparticles are formed by reduction of silver ions by the functional groups of the polymer without the addition or application of an external reducing agent.

The polymer used for preparing composites of the invention may have one or more functional groups capable of reducing silver ions to silver nanoparticles. The functional groups are not limited to any particular reducing functional groups. Examples include ester, ether, amine, imine, nitrile, epoxide, carboxyl, hydroxyl or carboxylic acid groups. Preferred functional groups are ester, hydroxyl, and amine groups. The polymer is preferably an acrylic, polyol, amine, or epoxy polymer. Examples include methyl acrylate polymers, ethyl acrylate polymers, butyl acrylate polymers, methyl methacrylate polymers, butyl methacrylate polymers, acrylonitrile polymers, polyether polyols, polyester polyols, polyamines, bisphenol A epoxy polymers and bisphenol F epoxy polymers.

An important aspect of the invention is that the coating of the invention is formed without the application or addition of an external reducing agent. This means that the reduction of silver ions to Ag nanoparticles occurs without using UV light or heat at a temperature of 100° C. or greater, or without the addition of an external reducing agent such as trisodium citrate, sodium borohydride, hydroxylamine hydrochloride, hydrazine, ascorbic add, ethylenediaminetetraacetic add (EDTA), polyvinylpyrrolidone, dimethylformamide, a plant extract, hydrogen gas.

It has previously been thought that an external reducing agent was required to form the Ag nanoparticles in situ and thus form the coating composites. The applicant has found that the composites can be formed using the inherent reducing capability of the polymer itself. The applicant additionally found that once formed the Ag nanoparticles are stabilised in the composite matrix by interaction with the functional groups of the polymer. Thus, in addition to avoiding the need to add or apply an external reducing agent, no external stabilising agent is needed. It was previously thought that formation of Ag nanoparticles in a polymeric composite material required the addition of an external stabilising or linking agent or the AgNPs would agglomerate leading to leaching and reduced effectiveness of the antimicrobial properties of the Ag nanoparticles, Examples of stabilisers include trisodium citrate, polyvinylpyrrolidone, polyvinyl alcohol, oleylamine, cetyl trimethylammonium bromide, poly(N-isopropylacrylamide), sugars, fatty acids, and sodium dodecyl sulfate. The coating of the invention can be prepared without the addition of any such stabiliser.

The silver ions used to form the Ag nanoparticles are typically in the form of an aqueous solution of silver nitrate, silver acetate, silver carbonate, silver perchlorate, silver phosphate, silver trifluoroacetate, silver benzoate, or silver lactate. Silver nitrate is the preferred silver salt, but any suitable silver salt may be used. Non-aqueous solutions of silver salts can also be used in the synthesis method.

Preferred coatings of the invention are acrylic emulsions and epoxy resins with silver concentrations in the range 0.01-5 wt %. They can also include amine hardeners, hindered amine light stabilisers and polyols. In epoxy resins, the amine functionality of the amine hardener and the epoxide and ether of the resin are electron rich functionalities which means that they are effective at reducing and stabilising Ag nanoparticles in situ.

In the case of the amine functionality, a one electron transfer from the amine reduces the $Ag^+$ to $Ag^0$. Ag nanoparticles form within the polymer and are then stabilised by remaining amine, imine, hydroxyl and ether functionalities. This process prevents bulk formation of Ag, restricting particle size to yield nanoparticles and microparticles of Ag, while forming strong associations between the polymer backbone and the Ag nanoparticles and microparticles.

In the aqueous environment of an acrylic emulsion of PMMA (polymethylmethacrylate), the emulsion becomes slightly acidified on addition of a silver salt such as $AgNO_3$. This leads to acid hydrolysis of ester groups of PMMA, which then leaves the PMMA ester in equilibrium with its carboxylic acid analogue (polymethacrylic acid) and methanol. The $Ag^+$ then oxidises the methanol to formaldehyde and is reduced to $Ag^0$. This forms the seeds for Ag nanoparticle growth which are in turn capped by the carboxyl functionality of the PMMA, restricting the reduction to bulk Ag formation, and forming a strong Ag nanoparticle acrylic composite material.

The composite of the invention has both antimicrobial and antifouling properties and can therefore prevent biofilm formation. Composites have been found to be antifungal and antiviral, as well as antibacterial. In particular, they have been shown to have a strong antimicrobial response against both Gram positive and Gram negative bacteria, including *E. coli, S. aureus* and *L. monocytogenes,* which continues after multiple washing cycles with several different cleaning solvents. This is due to the very low leach rate achieved by the strong association of the Ag nanoparticles. Consequently, the coating of the invention is useful for a variety of applications where is it desirable to prevent the adherence or growth of microbes, including for example on medical devices, heating, ventilating and air-conditioning units, ductwork and piping for air and other fluids, water reservoirs, walls, floor, and ceilings, and food and beverage manufacturing equipment or packaging.

The coating of the invention has been shown to prevent the growth of diatoms, a form of algae, and hence has application as an antifouling coating to any surface susceptible to fouling by algae. The coating has also been shown to reduce the settlement of the sea squirt *Ciona savignyi,* a common aquaculture biofouling organism. The coating may be used on any surface submerged in water, for example all or part of a vessel hull, a jetty or wharf structure, off-shore structure, or aquaculture equipment.

Examples 1 to 3 demonstrate methods of functionalising aqueous acrylic emulsions for different applications. The aqueous polymethylmethacrylate (PMMA) acrylic emulsion contains ester groups which upon addition of $AgNO_3$ are slightly acidified. It is considered that this leads to acid hydrolysis of the ester of PMMA. Acid hydrolysis then leaves the PMMA ester in equilibrium with the carboxylic acid, polymethylmethacrylic acid, and methanol. The $Ag^+$ then oxidises the methanol to formaldehyde, and is so reduced to $Ag^0$. The $Ag^0$ nanoparticles are stabilised by the carboxyl functionality of the PMMA resulting in a strong interaction between the Ag nanoparticles and the acrylic polymer. This synthesis method can be applied to base resins as well as formulated resins as demonstrated in the Examples where the fully formulated coatings of Enduracoat™ ACR-33-V and Solagard™ where successfully functionalised using the same synthesis method as used for the base resin Neocryl XK-98 (Example 1). The presence of pigments and fillers did not prevent successful reduction of the $Ag^+$ to Ag nanoparticles within the coatings by the PMMA, nor did it affect the antimicrobial activity exhibited by the coatings (Example 4).

The low leach rate of silver is demonstrated in Example 5. The strong association of the silver nanoparticles to the polymer backbone prevents leaching of the silver. The low leach rate provides a longer antimicrobial life time to the coating, while also mitigating any adverse environmental effects that can occur due to high concentrations of leached silver.

Example 6 demonstrates silver nanoparticle functionalisation of a 2-pot water-based epoxy coating Endurabond™ ECO 300. The diethylene triamine, triethylene tetramine, and modified polyamide hardener components of the epoxy resin provide primary and secondary amine functionality. It is likely that tertiary amines will also be present throughout the polymerisation process. It is considered that the amine functionality in the epoxy composition reduces the $Ag^+$ to $Ag^0$ through complexation and stabilisation of the $Ag^+$ followed by one electron transfer and oxidative dehydrogenation to reduce $Ag^+$ to $Ag^0$ and form an amine radical. The amine radical can in turn reduce a second $Ag^+$ and through deprotonation go on to form an imine. The resultant Ag nanoparticles are then capped and stabilised through the amine, imine and ether functionalities of the epoxy itself. In Example 6, both Part A and Part B hardener and resin were functionalised with Ag nanoparticles. It should be noted that functionalising either Part A or Part B, as well as both, can achieve a nanoparticle functionalised coating, demonstrating that the amine hardener and epoxy resin are both capable of reducing $Ag^+$ to $Ag^0$ forming silver nanoparticle composites.

Example 7 demonstrates the antimicrobial activity of Ag functionalised Endurabond™ ECO 300. As in Example 5, the zone of inhibition testing was carried out against *E. coli*. It was found that Ag functionalised Endurabond™ ECO 300 displayed a zone of inhibition where the antimicrobial activity of silver prevents the bacteria growing up to the sample. Unfunctionalised Endurabond™ ECO 300 did not display antimicrobial activity.

Ag leaching of Ag functionalised Endurabond™ ECO 300 was carried out in Example 8. As seen in Example 5, the strong association of the Ag nanoparticles with the polymer prevents leaching of the Ag demonstrating that low leaching is characteristic of the synthesis method and not restricted to the resin type.

In Example 9, Ag functionalised and unfunctionalised Neocryl™ XK-98 and Endurabond™ ECO 300 were tested in a diatom settlement assay. Diatoms are microscopic algae and an early stage marine fouling organism. Preventing microfouling delays macrofouling organisms from settling, providing marine antifouling activity. Analysis of the samples showed that when functionalised with Ag, the coatings prevented the settlement of diatoms, whereas unfunctionalised samples had surfaces covered in the microscopic algae.

The hindered amine light stabiliser Tinuvin™ 292 was functionalised with silver nanoparticles in Example 10. Here the amine functionality of the Tinuvin™ 292 is exploited to reduce $Ag^+$ to $Ag^0$. A possible reaction mechanism is that $Ag^+$ undergoes one electron reduction from the lone pair associated with the tertiary amine of the n-methyl piperidine. The Ag nanoparticles formed are then stabilised by the amine and ester functionalities of the bis(1,2,2,6,6-pentamethyl-4-piperidinyl)-sebacate and 1-(methyl)-8-(1,2,2,6,6-pentamethyl-4-piperidinyl)-sebacate. This example demonstrates that the method of nanoparticle functionalisation is not limited to only epoxy and acrylic based resin systems.

In Example 11, Ag functionalised and unfunctionalised Neocryl™ XK-98 were tested for their antifouling activity in a settlement bioassay against the sea squirt *Ciona savignyi*. The results showed that Ag functionalisation of the Neocryl™ XK-98 prevents the settlement of *C. savignyi* with all Ag functionalised samples showing 100% settlement inhibition. This bioassay demonstrates the ability of Ag functionalised composite resins to act as antifouling agents.

Example 12 used The Japanese Industrial Standard Committee method, JIS Z 2801, to test the antimicrobial activity of Ag functionalised Neocryl™ XK-98 against both Gram positive and Gram negative bacteria. The test organisms included *E. coli, S. aureus* and *L. monocytogenes*. Strong antimicrobial activity was exhibited by the Ag functionalised Neocryl™ XK-98 across a range of Ag concentrations. The experiment demonstrates the efficacy of Ag functionalisation of Neocryl™ XK-98 as an antimicrobial coating.

Example 13 describes a method of functionalising polyol blends for use in urethane resin systems. Ag functionalised urethane was achieved by polyol reduction of $Ag^+$ to $Ag^0$. This was followed by addition of an isocyanate hardener to crosslink the resin system and form the Ag nanoparticle urethane composite resin coating.

Example 14 describes the use of The Japanese Industrial Standard Committee method, JIS Z 2801, to test the antimicrobial activity of the Ag functionalised urethane against *S. aureus*. Strong antimicrobial activity was exhibited by the Ag functionalised urethane composite resin demonstrating its efficacy for use as an antimicrobial coating in urethane systems.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The invention is further described with reference to the following examples. It will be appreciated that the invention as claimed is not intended to be limited in any way by these examples.

EXAMPLES

Example 1

Self-Cross-Linking Poly(Methylmethacrylate) Emulsion

A self-cross-linking acrylic emulsion, Neocryl™ XK-98 (DSM Coatings) was functionalised using the following general synthesis method.

Figure 3:
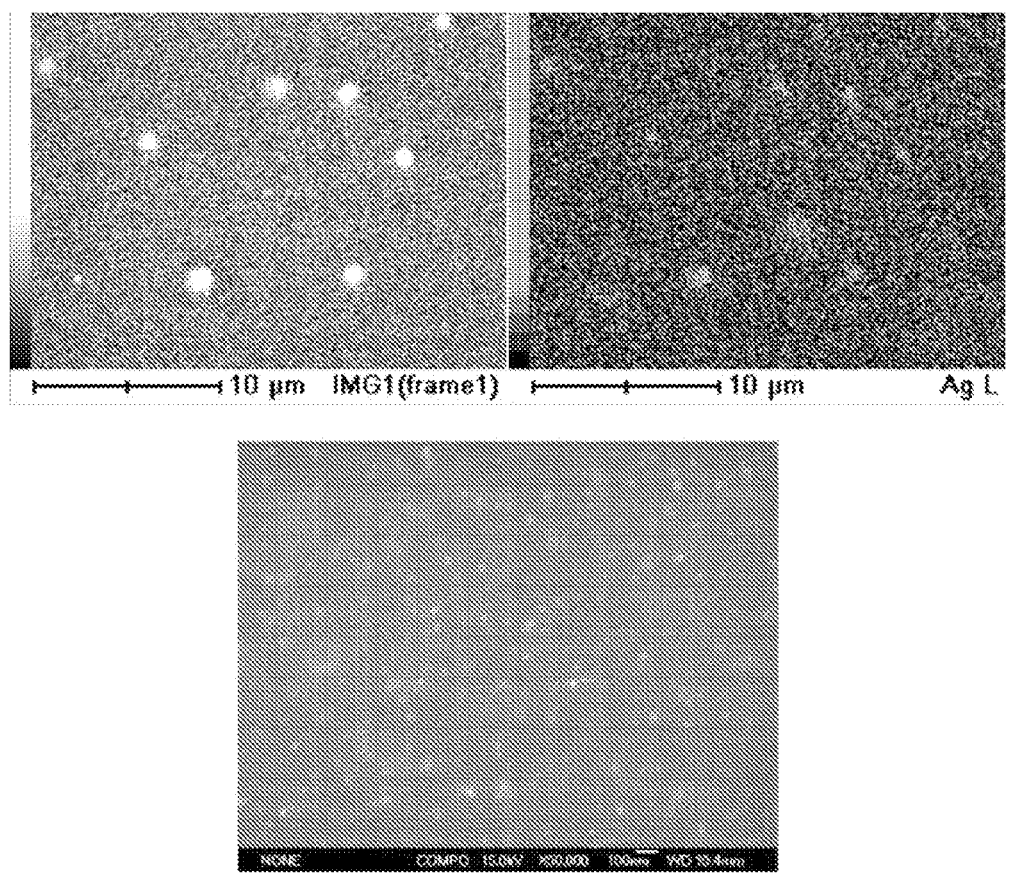
FIG. 3 shows SEM/EDS of Ag functionalised Neocryl™ XK-98.

Aqueous $AgNO_3$ (0.25 mL) was added to 5 g of Neocryl™ XK-98 at various concentrations to give a final Ag concentration in the Neocryl™ XK-98 of between 0.01% and 1%. The $AgNO_3$ was added slowly to the Neocryl™ XK-98 while under high shear overhead mixing to disperse the $AgNO_3$. The samples were then left to agitate on a shaking table overnight, during which time the samples containing Ag produced a colour change from clear to yellow/orange, and then to orange/brown. This is due to the phenomenon of localised surface plasmon resonance (LSPR) displayed by the Ag nanoparticles, and was confirmed by UV-vis spectroscopy, where the characteristic peak for Ag nanoparticles was observed (see FIG. 1). XRD analysis of the Ag functionalised Neocryl™ XK-98 showed a diffraction pattern for $Ag^0$ (see FIG. 3) indicating that the reduction of $Ag^+$ to $Ag^0$ was completed during the synthesis. Further, SEM/EDS analysis confirmed this showing well-dispersed Ag nanoparticles of a wide size distribution ranging from nano to microparticle size were produced in situ within the Neocryl™ XK-98.

A summary of the Ag Neocryl™ XK-98 concentrations produced, the characterisation techniques and observed results are shown in Table 1.

TABLE 1

Ag Neocryl™ XK-98 samples and characterisation

| | Sample Ag concentration (wt %) | | | | | | |
|---|---|---|---|---|---|---|---|
| | 0 | 0.01 | 0.02 | 0.1 | 0.25 | 0.5 | 1.0 |
| Colour change observed | No | Yes | Yes | Yes | Yes | Yes | Yes |
| UV-vis Ag LSPR band observed | No | No | Yes | Yes | Yes | Yes | Yes |
| XRD $Ag^0$ diffraction pattern observed | No | No | No | No | Yes | Yes | Yes |
| SEM/EDS confirms Ag in nano/micro particle form | No | Yes | Yes | Yes | Yes | Yes | Yes |

Example 2

Self-Cross-Linking Poly(Methylmethacrylate) Timber Stain

A self-cross-linking acrylic timber stain, Enduracoat™ ACR-33-V (Polymer Group Ltd) was functionalised using the general synthesis method of Example 1. A colour change was not observed because Enduracoat™ ACR-33-V is formulated with an $Fe_2O_3$ pigment giving the coating a deep red/brown colouration.

UV-vis spectroscopy was unable to conclusively confirm the presence of Ag nanoparticle LSPR peaks due to the strong $Fe_2O_3$ pigment absorption. However, XRD displayed a diffraction pattern for $Ag^0$ confirming the reduction of $Ag^+$, for samples of a concentration of greater than 0.25% due to instrument sensitivity. SEM/EDS analysis of the Ag Enduracoat™ ACR-33-V samples showed a range of Ag particles ranging from nano to microparticle size well-distributed throughout the Ag Enduracoat™ ACR-33-V timber stain.

TABLE 2

Ag Enduracoat™ ACR-33-V samples and characterisation

| | Sample Ag concentration (wt %) | | | | | |
|---|---|---|---|---|---|---|
| | 0 | 0.01 | 0.1 | 0.25 | 0.5 | 1.0 |
| Colour change observed | No | No | No | No | No | No |
| UV-vis Ag LSPR band observed | No | No | No | No | No | No |
| XRD $Ag^0$ diffraction pattern observed | No | No | No | Yes | Yes | Yes |
| SEM/EDS confirms Ag in nano/micro particle form | No | Yes | Yes | Yes | Yes | Yes |

Example 3

Water-Based Acrylic House Paint

A self-cross-linking acrylic exterior house paint Solagard™ (Wattyl) was functionalised using the general synthesis method of Example 1. A colour change was observed in the functionalised Solagard™ from white to purple to grey over this time. This difference in colour change compared to the Neocryl XK-98 is due to the high concentration of $TiO_2$ pigment used in the Solagard™ formulation.

UV-vis spectroscopy showed a redshifted absorbance indicative of Ag nanoparticles coupled with $TiO_2$ indicating Ag nanoparticle formation. This was further confirmed with XRD analysis which showed an $Ag^0$ diffraction present in higher concentration Ag samples.

SEM/EDS analysis showed Ag nanoparticles were formed during the synthesis method and well-distributed throughout the paint. It was noted that there was a high proportion of Ag nanoparticles closely associated to the $TiO_2$ pigment.

TABLE 3

Ag Solagard™ samples and characterisation

| | Sample Ag concentration (wt %) | | | | | |
|---|---|---|---|---|---|---|
| | 0 | 0.01 | 0.02 | 0.05 | 0.1 | 0.2 |
| Colour change observed | No | Yes | Yes | Yes | Yes | Yes |
| UV-vis Redshifted Ag LSPR band observed | No | Yes | Yes | Yes | Yes | Yes |
| XRD $Ag^0$ diffraction pattern observed | No | No | No | No | Yes | Yes |
| SEM/EDS confirms Ag in nano/micro particle form | No | Yes | Yes | Yes | Yes | Yes |

Example 4

Antimicrobial Activity of Neocryl™ XK-98

Figure 4:
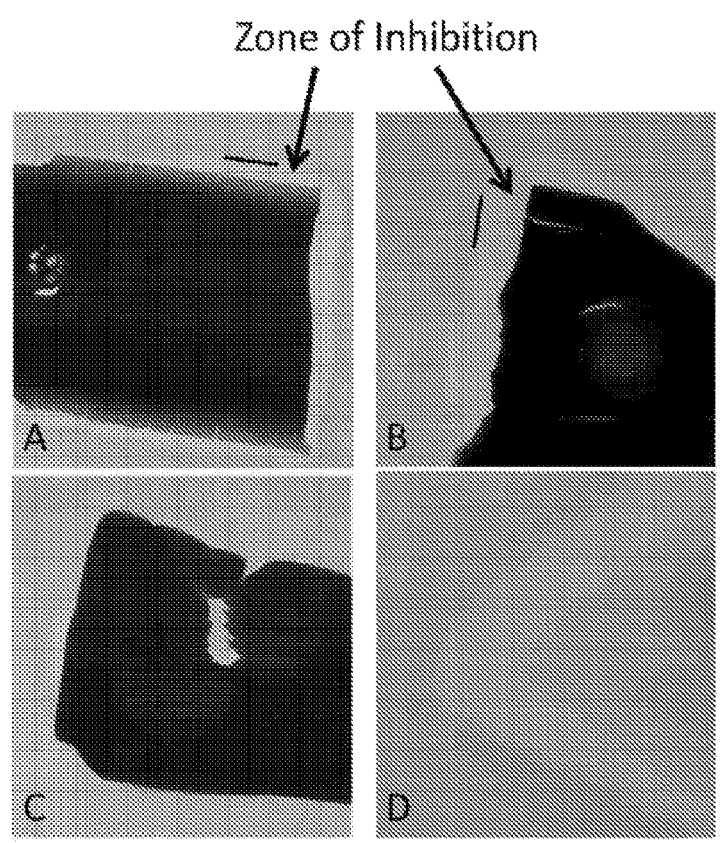
FIG. 4 shows zone of inhibition testing of A) 0.5% Ag Enduracoat™ ACR-33-V, B) 0.5% Ag Neocryl™ XK-98, C) untreated Enduracoat™ ACR-33-V, and D) untreated Neocryl™ XK-98.

*E. coli* is a common bacterium used in assays to assess the antimicrobial activity of materials. Zone of inhibition testing against *E. coli* showed that the Ag functionalised 0.5% Neocryl™ XK-98 and 0.5% Enduracoat™ ACR-33-V of Examples 1 and 2 exhibit strong antimicrobial activity when applied as a coating. FIG. 4 shows silver functionalised samples display a zone of inhibition where the Ag nanoparticles had prevented E. coli growing in proximity to the samples.

In addition to zone of inhibition testing, Ag functionalised Neocryl™ XK-98 was applied to a polymer substrate a surface coating and was assessed for antimicrobial activity against *E. coli* using the following method.

Samples were coated with 0.25% and 0.5% Ag functionalised Neocryl™ XK-98 (prepared according to Example 1) and washed with 70% IPA and rinsed with distilled water 7 times. The samples were then inoculated with 10 μl of bacterium before incubation for 24 hours, and CFU counted. Samples were tested in triplicate.

TABLE 4

Antimicrobial testing of plastics coated with Ag Neocryl™ XK-98

| Initial Bacteria Concentration (CFU) | Untreated Neocryl™ | 0.25% Ag Neocryl™ | 0.5% Ag Neocryl™ |
|---|---|---|---|
| 100 | 10 | 0 | 0 |
| 10000 | >2000 | 0 | 3 |
| 1000000 | >2000 | 2 | 0 |

Example 5

Silver Leach Rate for Ag Neocryl™ XK-98

Leaching tests of the 0.5% Ag Neocryl XK-98 samples were carried out by submerging and agitating the samples in distilled water at 35° C. in a shaking water bath. Samples of the leachate were taken every day over 7 days. These samples were then analysed for Ag using graphite furnace atomic absorption spectroscopy (GF-AAS). The results are shown in Table 5.

TABLE 5

Silver leaching of 0.5% Ag Neocryl™ XK-98

| Day | Silver concentration (ppb) |
|---|---|
| 1 | 0.03 |
| 2 | Not detected |
| 3 | Not detected |
| 4 | Not detected |
| 5 | Not detected |
| 6 | Not detected |
| 7 | Not detected |

Example 6

Water-Based Epoxy Coating

A water-based 2-pot epoxy coating Endurabond™ ECO 300 (Polymer Group Ltd) was functionalised with Ag nanoparticles. This was achieved by functionalising both the Part A and Part B components with Ag nanoparticles.

The Endurabond™ ECO 300 Part A was functionalised by following general synthesis method. $AgNO_3$ (0.5 mL) was added to 5 g of Endurabond™ ECO Part A under high shear mixing to give a final concentration of $Ag^+$ of between 0.1 and 2 wt % and left to agitate on a shaking table at 30 rpm for 4 hours. During this time the beige Endurabond™ ECO 300 Part A underwent a colour change to a yellow/brown indicating the formation of Ag nanoparticles.

Endurabond™ ECO 300 Part B was prepared by the addition 0.5 mL $AgNO_3$ dissolved in butyl carbitol to 5 g of Endurabond™ ECO 300 Part B, to give a concentration of between 0.1 and 2 wt % Ag. The $AgNO_3$ was added under high shear mixing and mixed for a further 5 min under high shear to ensure dispersion of the butyl carbitol. This was followed by agitation on a shaking table at 30 rpm overnight. During this time the Endurabond™ ECO Part B changed colour from a light yellow/orange to dark orange indicating that Ag nanoparticles had formed.

The Endurabond™ ECO 300 Part A and Part B were then mixed in the ratio of 4:1. The Ag functionalised Endurabond™ ECO 300 was an orange/brown colour darker than the beige of the untreated Endurabond™ ECO 300. This colour change indicated successful Ag nanoparticle functionalisation due to the LSPR effects of the nanoparticles.

XRD of the Ag functionalised Endurabond™ ECO 300 showed a diffraction pattern for $Ag^0$ confirming the reduction of $Ag^+$ during the synthesis.

SEM/EDS analysis showed Ag particles of nano and microparticles size were formed and well distributed throughout the coating.

TABLE 6

Ag Endurabond™ ECO 300 samples and characterisation

| | Sample Ag concentration (wt %) | | | | | | |
|---|---|---|---|---|---|---|---|
| | 0 | 0.01 | 0.05 | 0.25 | 0.5 | 1.0 | 2.0 |
| Colour change observed | No | Yes | Yes | Yes | Yes | Yes | Yes |
| UV-vis Ag LSPR band observed | No | No | Yes | Yes | Yes | Yes | Yes |
| XRD $Ag^0$ diffraction pattern observed | No | No | No | Yes | Yes | Yes | Yes |
| SEM/EDS confirms Ag in nano/micro particle form | No | Yes | Yes | Yes | Yes | Yes | Yes |

Example 7

Antimicrobial Activity of Epoxy coating

Zone of inhibition testing against *E. coli* showed that the Ag functionalised 0.5% Endurabond™ ECO 300 of Example 6 exhibited antimicrobial activity when applied as a coating. Silver Endurabond ECO 300 displays a zone of inhibition where the Ag nanoparticles had prevented *E. coli* growing up to the samples.

TABLE 7

Zone of inhibition testing of 0.5% Ag Endurabond™ ECO 300

| | Untreated Endurabond ECO 300 | 0.5% Ag Endurabond ECO 300 |
|---|---|---|
| Zone of Inhibition present | No | Yes |

Example 8

Silver Leach Rate for Ag Endurabond ECO 300 Coating

Leaching tests of the 0.5% Ag Endurabond™ ECO 300 samples were carried out by submerging and agitating the samples in distilled water at 35° C. in a shaking water bath. Samples of the leachate were taken every day over 7 days. These samples were then analysed for Ag using GF-AAS.

TABLE 8

Silver leaching of 0.5% Ag Endurabond™ ECO 300

| Day | Silver concentration (ppb) |
|---|---|
| 1 | 0.73 |
| 2 | 0.058 |
| 3 | 0.069 |
| 4 | 0.036 |
| 5 | 0.050 |
| 6 | 0.010 |
| 7 | 0.011 |

Example 9

Diatom Antifouling of Ag Nanoparticle Endurabond™ ECO 300 and Neocryl XK-98 Resins The Ag nanoparticle functionalised Neocryl™ XK-98 and Endurabond™ ECO 300 (Example 1 and Example 6) resins when immersed in seawater (Wellington, New Zealand) showed activity against the natural diatoms present. Polycarbonate squares were coated with Ag functionalised and unfunctionalised resin. These samples were then immersed in a diatom culture produced from seawater (Wellington, NZ) for 7 days in a shaking incubator. After 7 days the samples were analysed by fluorescence microscopy to observe diatom settlement, if any. Blank samples of unfunctionalised resins where covered in diatoms that had settled on the surface of the samples. In contrast, no diatoms had settled on the samples coated with 0.25% and 0.5% Ag functionalised resins. Samples showed that under the same conditions the Ag functionalisation prevents the settlement of the diatoms, providing antifouling protection in the marine environment. Diatoms are a microscopic slime fouler, it has been shown that prevention of these microfoulers can inhibit the settlement of macrofouling.

TABLE 9

Diatom settlement testing against Ag functionalised Endurabond™ ECO 300 and Neocryl™ XK-98

|  | Untreated Endurabond™ ECO 300 | 0.25% Ag Endurabond™ ECO 300 | 0.5% Ag Endurabond™ ECO 300 | Untreated Neocryl™ XK-98 | 0.25% Ag Neocryl™ XK-98 | 0.5% Ag Neocryl™ XK-98 |
|---|---|---|---|---|---|---|
| Diatoms present | Yes | No | No | Yes | No | No |

Example 10

Ag Nanoparticle Tinuvin™ 292 Hindered Amine Light Stabiliser

Tinuvin™ 292 is a commercially available mixture of two hindered amine light stabilisers (HALS) and is a pale yellow viscous oil. $AgNO_3$ was dissolved in butyl carbitol. 0.25 mL of the solution was added under high shear mixing to 5 g of Tinuvin™ 292 to give a concentration of $Ag^+$ in the composite of 0.005 or 0.01%. The samples were then agitated on a shaking table at overnight. A colour change from pale yellow to orange occurred 30 min to 1 hour after the addition of $Ag^+$ and then proceeded from orange to orange/brown overnight. This colour change is indicative of Ag nanoparticle formation within the HALS and shows increasing reduction of $Ag^+$ to $Ag^0$ over the period of the reaction time and the development of LSPR from the Ag nanoparticles. This was confirmed by Cryo SEM and TEM analysis showing the formation of spherical silver nanoparticles within the HALS. Silver nanoparticle functionalised Tinuvin™ 292 therefore has potential to be used in resin formulations as an antimicrobial and UV stabilising agent.

Example 11

Ciona savignyi Antifouling Bioassay

The *C. savignyi* bioassay followed the method described by Cahill et al. 2013.[10] Adult *C. savignyi* were collected from Nelson Marina (Nelson, New Zealand) and held in a controlled temperature (18±1° C.) recirculating seawater system under constant light for 7 days until competent to spawn. Eggs and sperm were dissected from 6 individuals using sharpened Pasteur pipettes, and transferred separately to 50 mL glass Petri dishes filled with 25 mL and 50 mL of reconstituted seawater (RSW), respectively. Eggs from each individual were cross-fertilised with eight drops of sperm suspension from each of two other individuals. After 1 h the eggs were sieved (10 micron), rinsed three times with RSW to remove excess sperm, transferred to fresh glass Petri dishes filled with 25 mL RSW, and held at 18±1° C. for 18 h to hatch. Hatched larvae from the 6 individuals were pooled, and then diluted with additional RSW in a 1 L glass beaker to yield a larval suspension containing 7 larvae/mL. The larval suspension was mixed with a magnetic stirrer and aliquoted into 6-well tissue culture plates containing the Neocryl™ coated discs. Plates were held at 18±1° C. for 5 days, and then the number of successfully metamorphosed juveniles adhered to the discs were counted using a dissecting microscope. Antifouling activity was calculated as % inhibition of the number of larvae that had successfully adhered and completed metamorphosis after 5 days in treatments (LT) vs blank controls (LBC) according to the following formula:

Inhibition of settlement and metamorphosis=$\frac{LT-LBC}{LT} \times 100$

TABLE 10

Inhibition of *C. savignyi* by Ag functionalised Neocryl™ XK-98

|  | Untreated Neocryl™ XK-98 | 0.25% Ag Neocryl™ XK-98 | 0.5% Ag Neocryl™ XK-98 | 1% Ag Neocryl™ XK-98 |
|---|---|---|---|---|
| % Inhibition | 0% | 100% | 100% | 100% |

Example 12

Antimicrobial Activity of Neocryl™ XK-98

Quantitative antimicrobial testing of Ag functionalised Neocryl™ XK-98 was tested against *E. coli, S. aureus* and *L. monocytogenes* using the standard method The Japanese Industrial Standard Committee method JIS Z 2801. The general method for JIS Z 2801 is as follows. The test microorganism is prepared, usually by growth in a liquid culture medium. The suspension of test microorganism is standardised by dilution in a nutritive broth (this affords microorganisms the opportunity to proliferate during the test). Control and test surfaces are inoculated with microorganisms, and then the microbial inoculum is covered with a thin, sterile film. Covering the inoculum spreads it, prevents it from evaporating, and ensures close contact with the antimicrobial surface. Microbial concentrations are determined at "time zero" by elution followed by dilution and plating to agar. A control is run to verify that the neutralisation/elution method effectively neutralises the antimicrobial agent in the antimicrobial surface being tested. Inoculated, covered control and antimicrobial test surfaces are allowed to incubate undisturbed in a humid environment for 24 hours, usually at body temperature. After incubation, microbial concentrations are determined. Reduction of microorganisms relative to the control surface is calculated. The results are shown in Tables 11-13.

TABLE 11

Antimicrobial effect on *S. aureus*

|  | Reduction Compared to Control at Time Zero |
|---|---|
| Unfunctionalised Neocryl™ XK-98 | 95.86% |
| 0.1% Ag functionalised Neocryl™ XK-98 | >99.997% |
| 0.25% Ag functionalised Neocryl™ XK-98 | >99.997% |
| 0.5% Ag functionalised Neocryl™ XK-98 | >99.998% |

TABLE 12

Antimicrobial effect on *E. coli*

| | Reduction Compared to Control at Time Zero |
|---|---|
| Unfunctionalised Neocryl ™ XK-98 | 98.38% |
| 0.1% Ag functionalised Neocryl ™ XK-98 | >99.998% |
| 0.25% Ag functionalised Neocryl ™ XK-98 | >99.998% |
| 0.5% Ag functionalised Neocryl ™ XK-98 | >99.998% |

TABLE 13

Antimicrobial effect on *L. monocytogenes*

| | Reduction Compared to Control at Time Zero |
|---|---|
| Unfunctionalised Neocryl ™ XK-98 | 99.89% |
| 0.1% Ag functionalised Neocryl ™ XK-98 | >99.99994% |
| 0.25% Ag functionalised Neocryl ™ XK-98 | >99.99994% |
| 0.5% Ag functionalised Neocryl ™ XK-98 | >99.99994% |

Example 13

Functionalisation of Urethane

A 100% solids 2-part urethane coating (Polymer Group Ltd) was functionalised with Ag nanoparticles. This was achieved by functionalising the polyester-ether polyol and glycol ether blend resin component with Ag nanoparticles before addition of the polyisocyanate blend hardener. The polyester-ether polyol and glycol ether blend resin was functionalised by following general synthesis method. $AgNO_3$ (0.5 mL) was added to 5 g of resin under high shear mixing to give a final concentration of $Ag^+$ of between 0.1 and 0.6 wt % and left to agitate on a shaking table at 30 rpm for 4 hours. During this time the resin underwent a colour change to a yellow/brown indicating the formation of Ag nanoparticles. The resin and polyisocyanate blend hardener were then mixed in the ratio of 1:1.15 by mass. The Ag functionalised urethane was dark brown in colour unlike the beige colour of the untreated urethane. This colour change was due to successful Ag nanoparticle functionalisation due to the LSPR effects of the nanoparticles. XRD of the Ag functionalised polyurethane showed a diffraction pattern for $Ag^0$ confirming the reduction of $Ag^+$ during the synthesis. SEM/EDS analysis showed Ag particles of nano and microparticles size were formed and well distributed throughout the coating. The results are shown in Table 14.

TABLE 14

Formation of Ag functionalised polyurethane

| Sample Ag concentration (wt %) | 0 | 0.1 | 0.2 | 0.6 |
|---|---|---|---|---|
| Colour change observed | No | Yes | Yes | Yes |
| UV-vis Ag LSPR band observed | No | Yes | Yes | Yes |
| XRD $Ag^0$ diffraction pattern observed | No | Yes | Yes | Yes |
| SEM/EDS confirms Ag in nano/micro particle form | No | Yes | Yes | Yes |

Example 14

Antimicrobial Activity of Ag Functionalised Urethane Coating

Quantitative antimicrobial testing of Ag functionalised urethane from the Example 13 functionalisation of polyol resin was tested against *S. aureus* using The Japanese Industrial Standard Committee method JIS Z 2801 as described above for Example 12. The results are shown in Table 15.

TABLE 15

Antimicrobial effect on *S. aureus*

| | Reduction Compared to Control at Time Zero |
|---|---|
| Unfunctionalised urethane | 6.07% |
| 0.1% Ag functionalised urethane | 99.98% |

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

REFERENCES

1. Lee, P. & Meisel, D. Adsorption and surface-enhanced Raman of dyes on silver and gold sols. *J. Phys. Chem.* 60439, 3391-3395 (1982).

2. Xiong, Y. et al. Poly(vinyl pyrrolidone): a dual functional reductant and stabilizer for the facile synthesis of noble metal nanoplates in aqueous solutions. *Langmuir* 22, 8563-8570 (2006).

3. Hoppe, C. E., Lazzari, M., Pardiñas-Blanco, I. & Lopez-Quintela, M. A. One-step synthesis of gold and silver hydrosols using poly(N-vinyl-2-pyrrolidone) as a reducing agent. *Langmuir* 22, 7027-7034 (2006).

4. Chen, M. et al. Silver nanoparticles capped by oleylamine: formation, growth, and self-organization. *Langmuir* 23, 5296-5304 (2007).

5. Silva, A. M. B., de Araújo, C. B., Santos-Silva, S. & Galembeck, A. Silver nanoparticle in situ growth within crosslinked poly(ester-co-styrene) induced by UV irradiation: aggregation control with exposure time. *J. Phys. Chem. Solids* 68, 729-733 (2007).

6. Cheng, W. T., Chih, Y. W. & Yeh, W. T. In situ fabrication of photocurable conductive adhesives with silver nano-particles in the absence of capping agent. *Int. J. Adhes. Adhes.* 27, 236-243 (2007).

7. Sangermano, M., Yagci, Y. & Rizza, G. In situ synthesis of silver-epoxy nanocomposites by photoinduced electron transfer and cationic polymerization processes. *Macromolecules* 6, 8827-8829 (2007).

8. Kim, J. Y., Shin, D. H. & Ihn, K. J. Synthesis of poly(urethane acrylate-co-styrene) films containing silver nanoparticles by a simultaneous copolymerization/in situ electron transfer reaction. *Macromol. Chem. Phys.* 206, 794-801 (2005).

9. Cheng, Y.-J. et al. In situ formation of silver nanoparticles in photocrosslinking polymers. *J. Biomed. Mater. Res. B. Appl. Biomater.* 97, 124-131 (2011).

10. Cahill, P. L., Heasman, K., Jeffs, A. & Kuhajek, J. Laboratory assessment of the antifouling potential of a soluble-matrix paint laced with the natural compound polygodial. *Biofouling* 29, 967-975 (2013).

The invention claimed is:

1. A method for preparing a composite resin for coating a surface, the method comprising reacting a polymer with silver ions to reduce the silver ions to generate silver nanoparticles in situ before a curing step of the polymer, provided that no external reagent for reducing silver ions to metallic silver nanoparticles is added or applied, and wherein the polymer is selected from an acrylic polymer, polyol polymer, or epoxy polymer.

2. The method of claim 1, further provided that no stabiliser for preventing or minimising agglomeration of silver nanoparticles is added.

3. The method of claim 1, wherein the silver ions are provided as a solution of silver ions.

4. The method of claim 1, wherein the polymer and silver ions are reacted at a temperature of less than 100° C.

5. The method of claim 1, wherein the composition has a $Ag^0$ concentration of at least 0.01 wt %.

6. The method of claim 1, having a $Ag^0$ concentration of between 0.01 wt % and 5 wt %.

7. The method of claim 1, wherein the composition has a $Ag^0$ concentration of between 0.01 wt % and 0.5 wt %.

8. The method of claim 1, wherein the silver ions are provided as a solution of a silver salt.

9. The method of claim 8, wherein the silver salt is selected from the group comprising silver nitrate, silver acetate, silver carbonate, silver perchlorate, silver phosphate, silver trifluoroacetate, silver benzoate, and silver lactate.

10. The method of claim 1, wherein the polymer is selected from the group comprising methyl acrylate, ethyl acrylate, butyl acrylate, methyl methacrylate, butyl methacrylate, acrylonitrile, polyether polyol, polyester polyol, polycarbonate polyol, poly(meth)acrylate polyol, bisphenol A epoxy, and bisphenol F epoxy polymer.

* * * * *